US008475757B2

(12) United States Patent
Bublitz (10) Patent No.: US 8,475,757 B2
(45) Date of Patent: Jul. 2, 2013

(54) AGENTS FOR CARBON DIOXIDE CAPTURE, AGENTS FOR AMINE STABILIZATION AND METHODS OF MAKING AGENTS FOR CARBON DIOXIDE CAPTURE AND AMINE STABILIZATION

(75) Inventor: Mark Owen Bublitz, South Slocan (CA)

(73) Assignee: Pro-Con International, LLC, Daisetta, TX (US)

( * ) Notice: Subject to any disclaimer, the term of this patent is extended or adjusted under 35 U.S.C. 154(b) by 117 days.

(21) Appl. No.: 12/657,939

(22) Filed: Jan. 28, 2010

(65) Prior Publication Data

US 2010/0256347 A1 Oct. 7, 2010

Related U.S. Application Data

(60) Provisional application No. 61/167,337, filed on Apr. 7, 2009.

(51) Int. Cl.
*C01B 33/32* (2006.01)
*C01C 1/00* (2006.01)
*B01J 21/16* (2006.01)
*B01J 25/02* (2006.01)
*B01J 23/74* (2006.01)
*B01J 23/745* (2006.01)
*B01J 23/755* (2006.01)

(52) U.S. Cl.
USPC ........... 423/348; 423/325; 423/332; 423/352; 502/232; 502/240; 502/243; 502/301; 502/325; 502/337; 502/338

(58) Field of Classification Search
USPC .......... 423/325, 332, 348, 352, 413; 502/232, 502/240, 243, 301, 325, 337, 338
See application file for complete search history.

(56) References Cited

U.S. PATENT DOCUMENTS 4,029,747 A 6/1977 Merkl
4,234,547 A 11/1980 Urban
(Continued)

FOREIGN PATENT DOCUMENTS

CA 2578281 2/2005
EP 0492508 7/1992
(Continued)

OTHER PUBLICATIONS

Bobbert et al., "Solvation and Chemical Reaction of Sodium in Water Clusters", The European Physical Journal D, Dec. 2000, 3 pages.
(Continued)

*Primary Examiner* — Daniel C McCracken
*Assistant Examiner* — Daniel Berns
(74) *Attorney, Agent, or Firm* — Wells St. John P.S.

(57) ABSTRACT

Amine stabilizing agents containing an azeotrope comprising water, an alcohol, and sodium hydride. Amine stabilizing agents containing water and a liquid silica hydroxide compound. Methods of making of amine stabilizing agents where solid silicon rock and sodium hydroxide are mixed with an ammonium/water solution to produce a green liquid in a first stage of the reaction. Alcohol is added and the alcohol fraction is separated from the non-alcohol fraction to produce an alcohol fraction product and a bottom fraction that is not soluble in alcohol or organics. The agents can be added to amines for stabilizing amines in anime processing of gases, in $CO_2$ capture, in $CO_2$ abatement systems and in other systems where amines are utilized to remove contaminants.

17 Claims, 7 Drawing Sheets
(2 of 7 Drawing Sheet(s) Filed in Color)

U.S. PATENT DOCUMENTS

| | | |
|---|---|---|
| 4,571,328 A | 2/1986 | Rice |
| 4,957,639 A | 9/1990 | Fox |
| 5,229,030 A | 7/1993 | Clubley |
| 5,294,371 A | 3/1994 | Clubley |
| 6,962,955 B2 | 11/2005 | Kusudou et al. |
| 7,951,347 B2 | 5/2011 | Johnson |
| 7,988,831 B2 | 8/2011 | Hsu et al. |
| 8,119,091 B2 | 2/2012 | Keith |
| 8,167,979 B2 | 5/2012 | Hintz |
| 2003/0059361 A1 | 3/2003 | Carberry |
| 2009/0008608 A1 | 1/2009 | Bublitz et al. |
| 2010/0256347 A1 | 10/2010 | Bublitz |
| 2012/0040822 A1 | 2/2012 | Perez-Romo et al. |

FOREIGN PATENT DOCUMENTS

| | | |
|---|---|---|
| WO | PCT/IB2010/001745 | 11/2010 |
| WO | PCT/IB2010/001745 | 7/2012 |
| WO | PCT/US13/25636 | 4/2013 |

OTHER PUBLICATIONS

Shirahata et al., "Advanced Research on the Health Benefit of Reduced Water", Trends in Food Science & Technology 23 (2012) pp. 124-131.

AGENTS FOR CARBON DIOXIDE CAPTURE, AGENTS FOR AMINE STABILIZATION AND METHODS OF MAKING AGENTS FOR CARBON DIOXIDE CAPTURE AND AMINE STABILIZATION

RELATED PATENT DATA

This application claims priority under 35 U.S.C. §119 to U.S. Provisional Application Ser. No. 61/167,337 which was filed Apr. 7, 2009.

TECHNICAL FIELD

The present invention relates to methods of forming chemical agents for stabilizing amines, agents for stabilizing amines and assisting in $CO_2$ capture, methods of stabilizing amines, methods of $CO_2$ capture and abatement, and systems for $CO_2$ removal from gas streams and gas emissions.

BACKGROUND OF THE INVENTION

Amine treatment plants utilize amine processing to treat gas streams such as natural gas streams and refinery streams for removal of contaminants such as $CO_2$ and $H_2S$. The $CO_2$ captured during the amine processing can often be collected for commercial use. The amine utilized for amine treatment is often one of monoethanolamine (MEA), methyldiethanolamine (MDEA) or diethanolamine (DEA). Other amines utilized include diglycolamine (DGA), diisopropanolamine (DIPA) and proprietary amine agents.

Amine treatment for $CO_2$ capture can also be used to remove $CO_2$ from combustion gases, flue gases and abatement of greenhouse gases.

Problems associated with amine treatment include corrosion that can occur when $CO_2$ reacts with water in the amine solution to form acids. Other problems include foaming in the system, degradation of the amine mixture to form acids, bases and salts, and hydrocarbon saturation of the amine mixture. Additional problems include the high cost of amine or amine mixtures and high cost of regeneration.

It would be advantageous to develop agents for decreasing or preventing some or all of the problems associated with amine treatment set forth above.

SUMMARY OF THE INVENTION

The invention encompasses amine-stabilizing agents containing An azeotrope comprising water, an alcohol, and sodium hydride. The invention additionally encompasses amine stabilizing agents containing water and a liquid silica hydroxide compound. The invention additionally encompasses making of amine stabilizing agents. Solid silicon rock and sodium hydroxide are mixed with an ammonium/water solution to produce a green liquid in a first stage of the reaction. Alcohol is added and the alcohol fraction is separated from the non-alcohol fraction to produce an alcohol fraction product and a bottom fraction that is not soluble in alcohol or organics.

The agents can be added to amines for stabilizing amines in amine processing of gases, in $CO_2$ capture, in $CO_2$ abatement systems and in other systems where amines are utilized to remove contaminants.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Preferred embodiments of the invention are described below with reference to the following accompanying drawings.

FIG. 6 shows a chart of groups identifiable by infra-red analysis superimposed upon an infrared scan chart (Panel A), and in Panel B, an FTIR spectra comparison of the base product of the invention after reaction stage 1 (dashed) compared to the polymeric species product (solid) disclosed by Merkl in U.S. Pat. No. 4,029,747 (see Merkl, FIG. 7).

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

In general, the invention encompasses agents that stabilize amines in solution, methods of forming the agents and methods of utilizing the agents. The agents of the invention are useful in systems where amine treatment is utilized for removal of $CO_2$ and/or $H_2S$. More specifically, the agents can be utilized for treatment of natural gas, liquid petroleum gas, combustion gas, flue gases, etc. The agents of the invention can also be utilized for $CO_2$ capture to produce $CO_2$ for commercial use. The agents of the invention can additionally be utilized to stabilize amines in solution, including DNA.

Figure 1:
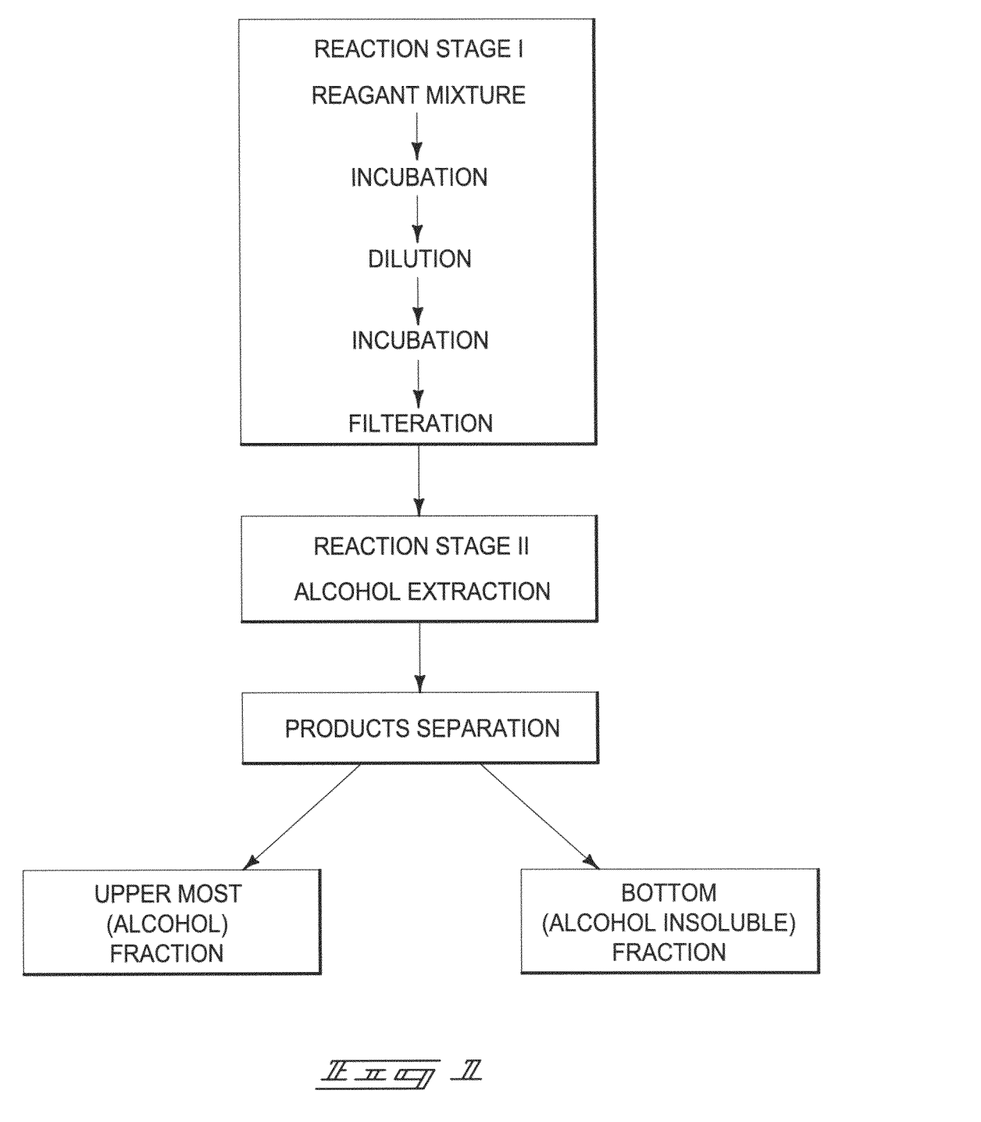
FIG. 1 is a flowchart diagram overview of methodology in accordance with one aspect of the invention.

Methods of producing agents of the invention are described generally with reference to FIGS. 1-4. Referring initially to FIG. 1, a reagent mixture is formed. An open reaction vessel is provided. Solid silicon in the form of silicon rock is added to the vessel. The size of the silicon rock utilized will be dependent upon the size of the reaction vessel as such affects the heating of the reaction. In a 35 gallon reaction, the average rock size should be about 2 inches diameter and larger. For a 300 gallon reaction, the average rock size should be 4 inches diameter and larger. 98% purity silicon metal may be utilized.

Solid NaOH is added in the form of flakes prills, or pellets. An appropriate ratio of silicon rock to NaOH can be from about 2:1 to about 5:12, by volume. While mixing quickly, a first water-ammonium solution is added to a final concentration of two parts water to one part NaOH, by volume, to form a mixture. The first water ammonium solution contains 5% ammonium hydroxide, mole weight. The ammonium solution is utilized to maintain the reaction temperature at or below 195.degree. F. The addition of ammonium to the mixture introduces free hydrogen, free electron presence and controls heat dissociation of water/sodium hydroxide.

In preferred embodiments a catalyst can be utilized. Appropriate catalysts include, for example, Fe—Ni catalysts and Raney nickel. Where an iron-nickel catalyst is utilized an example catalyst can be 2 grams of iron/nickel oxide per gallon.

Figure 2:
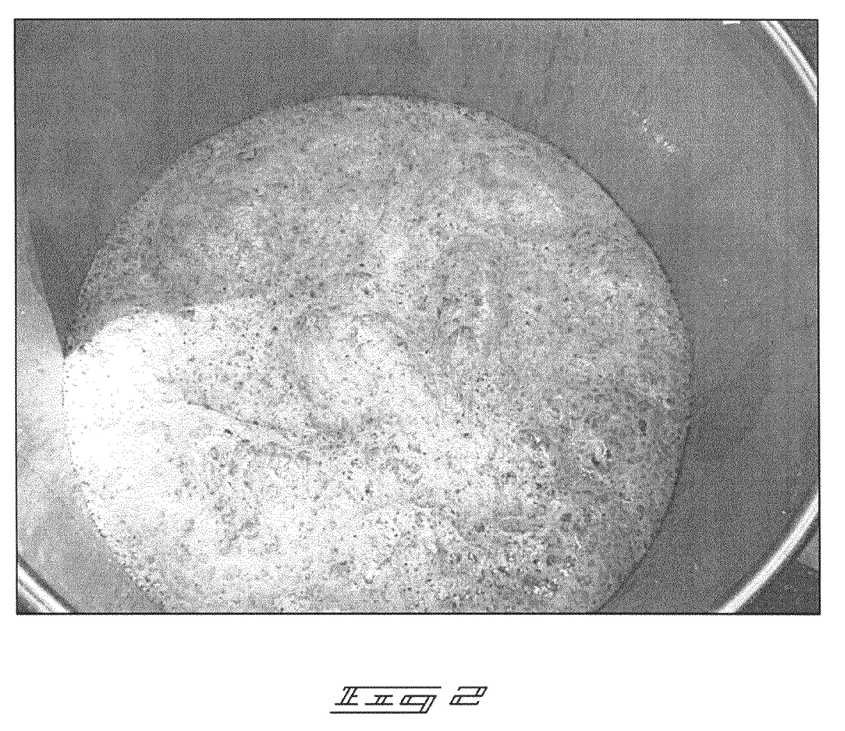
FIG. 2 shows the reaction of the invention occurring during "reaction stage 1.

The reaction mixture is allowed to react for a one to two hour incubation period. At about 30 minutes, the reaction will begin to fizz. At about 145° F., the reaction appears to boil. The reaction mixture is very viscous and appears as shown in FIG. 2.

After reacting from about one to two hours, a second water-ammonium solution is added in small aliquots. The second ammonium solution contains 10% ammonium hydroxide, mole weight. The amount of solution added is the minimum sufficient to maintain the temperature of the reaction mixture at or below 195° F. Addition of too much water will kill the reaction. Water-ammonium addition is discontinued upon reaching a four to one ratio of water to sodium hydroxide.

Figure 3:
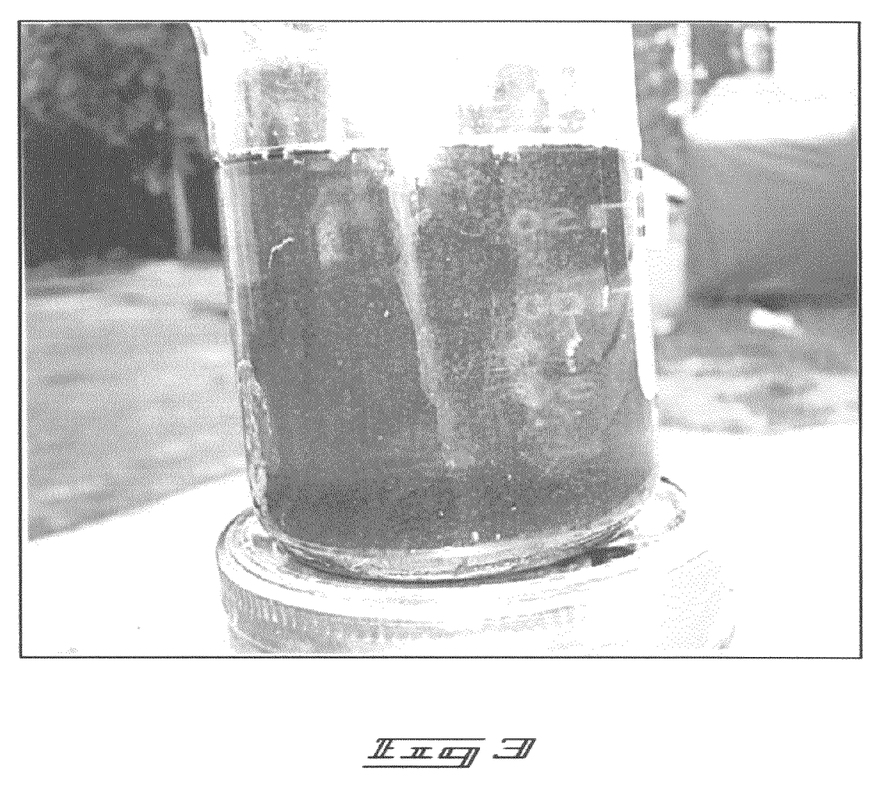
FIG. 3 shows the final product created by "reaction stage 1" of the invention.

The reaction mixture is allowed to continue to react for from about six to about 8 hours. Upon completion, the reaction mixture will discontinue foaming and be grey/green in appearance as shown in FIG. 3. And has a pH of greater than 14. Water is then added to dilute the mixture and to bring the mixture to a final density of about 1.3 specific gravity. The mixture is allowed to stand for a period of about 24 hours.

After standing, the reaction mixture is filtered to remove the remaining silicon rocks. The filtered product is a green liquid as shown in FIG. 3.

In prior art reference U.S. Pat. No. 4,029,747, issued to Merkl on Jun. 14, 1977, non-alkaline metal was reacted with an alkali metal hydroxide in the presence of aqueous ammonium. In the Merkl reference, the products were a monomeric metal amide complex and an inorganic polymeric complex. The products of the Merkl reference were analyzed by FTIR. The green base product after stage I of the present invention was analyzed by FTIR and a comparison was made to the FTIR spectra presented in Merkl to distinguish the resulting product from that disclosed by Merkl.

Figure 7:
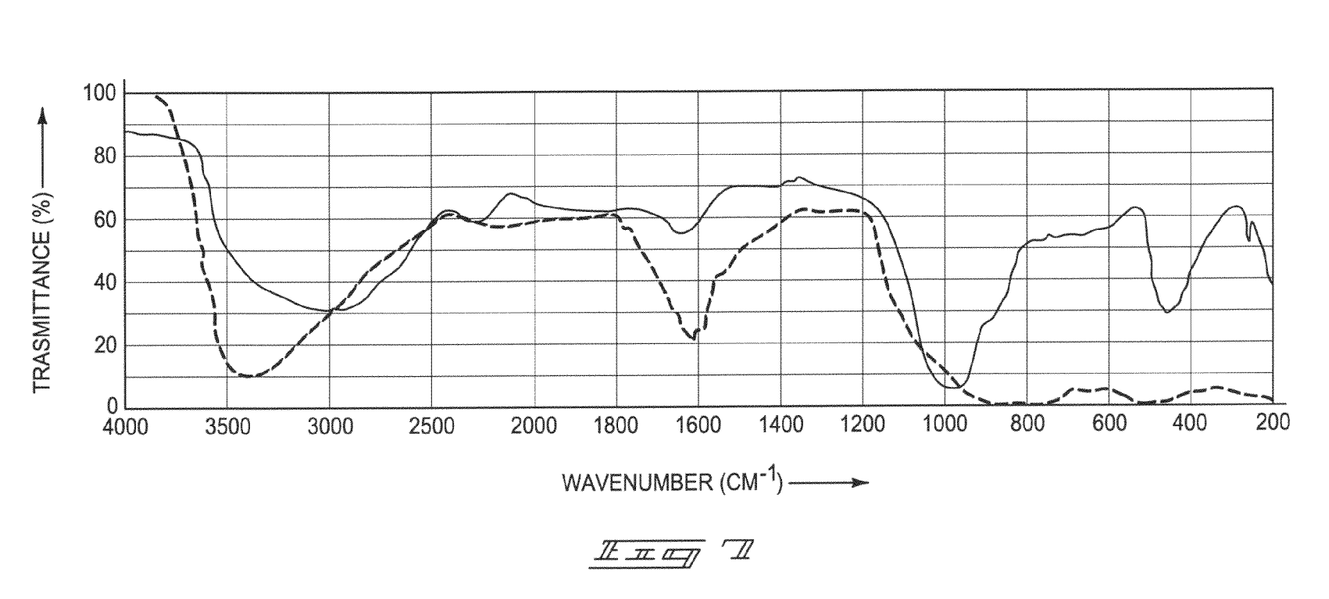
FIG. 7 shows FTIR spectra comparisons of the base product after reaction stage 1 (dashed) compared to the monomeric species product (solid) disclosed by Merkl in U.S. Pat. No. 4,029,747 (see Merkl at FIG. 3).

Referring to FIG. 6, such shows a comparison of the FTIR spectrum of the polymeric product of Merkyl (Si—Na liquid system after exothermic phase of reaction) shown in solid, and the FTIR spectrum of the stage I product of the invention, shown in dashed. In FIG. 7, the FTIR spectrum of the stage I product (dashed) is compared to the monomeric product disclosed in Merkl (solid). The comparison confirms that the product of the invention is not the metal amide complex or polymeric complex formed utilizing the methodology disclosed in the Merkyl patent.

As shown in FIG. 1, the resulting green liquid is mixed with an alcohol. Alternative volumes of alcohol may be utilized to produce varying product concentration in the alcohol fraction (see below). The volume of alcohol can be from about 10% to about 90%, preferably from about 33% to about 66% of the final alcohol mixture. In particular instances, it can be preferred to add a 50% final volume of alcohol to the green liquid.

The alcohol is not limited to a particular alcohol. In preferred aspects the alcohol can be selected from methanol, ethanol and isopropanol, most preferably ethanol. The resulting mixture is mixed vigorously for five minutes and allowed to stand for at least 24 hours.

Figure 4:
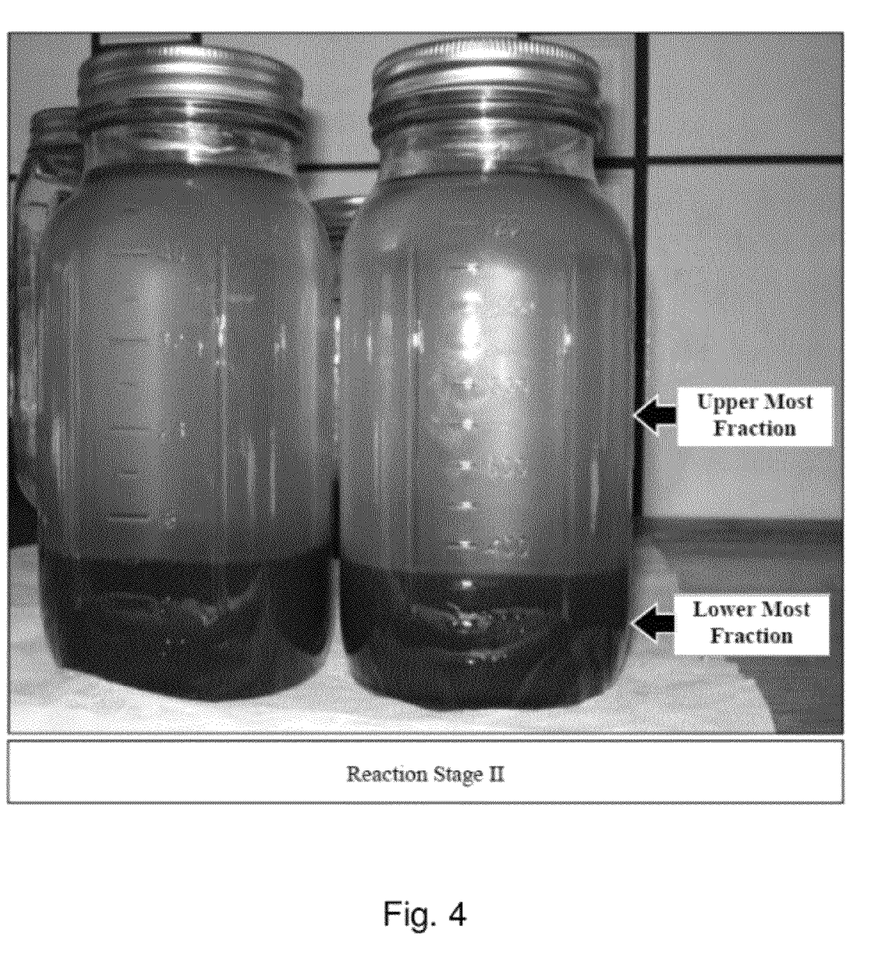
FIG. 4 shows the product separation in "reaction stage 2" before separating "upper most fraction" from "bottom fraction" of the invention.

Upon standing, the mixture visibly separates into two distinct product fractions as shown in FIG. 4. 50% of the green liquid is solubilized in alcohol and is present in the upper fraction while 50% is insoluble in alcohol. The uppermost fraction is clear and yellow in appearance with a pH of at least about 13.5, while the bottom fraction (heel) is black and viscous with a pH of greater than or equal to 14. The bottom fraction is insoluble in alcohol.

The two fractions are separated from one another and each are collected as a raw product. The uppermost fraction is filtered prior to use.

Each of the uppermost fraction product and bottom fraction product can be utilized to treat fluids for $CO_2$ removal. The product is added to an amine to form an amine mixture and the amine mixture is utilized to contact a fluid that contains $CO_2$ to be removed. The fluid can be a gas stream or an emission. The contacting allows $CO_2$ absorption. Regeneration processing, typically by heating, is conducted to release the $CO_2$ and regenerate the amine.

Considering first the uppermost (alcohol) fraction, such product contains a sodium hydride that is contained within liquid water crystals. Alternatively described, the product is an electromagnetic liquid water crystal containing a stable sodium hydride compound stabilized within, surrounded by an alcohol/water mixture.

The alcohol fraction is an azeotrope having a boiling point of about 80.5° C., above that of ethanol and lower than that of water. The hydride is an important part of this ternary azeotrope, affecting the boiling point of the alcohol fraction. The presence of the sodium hydride also affects hydrogen bond strengths and lengths.

Figure 5:
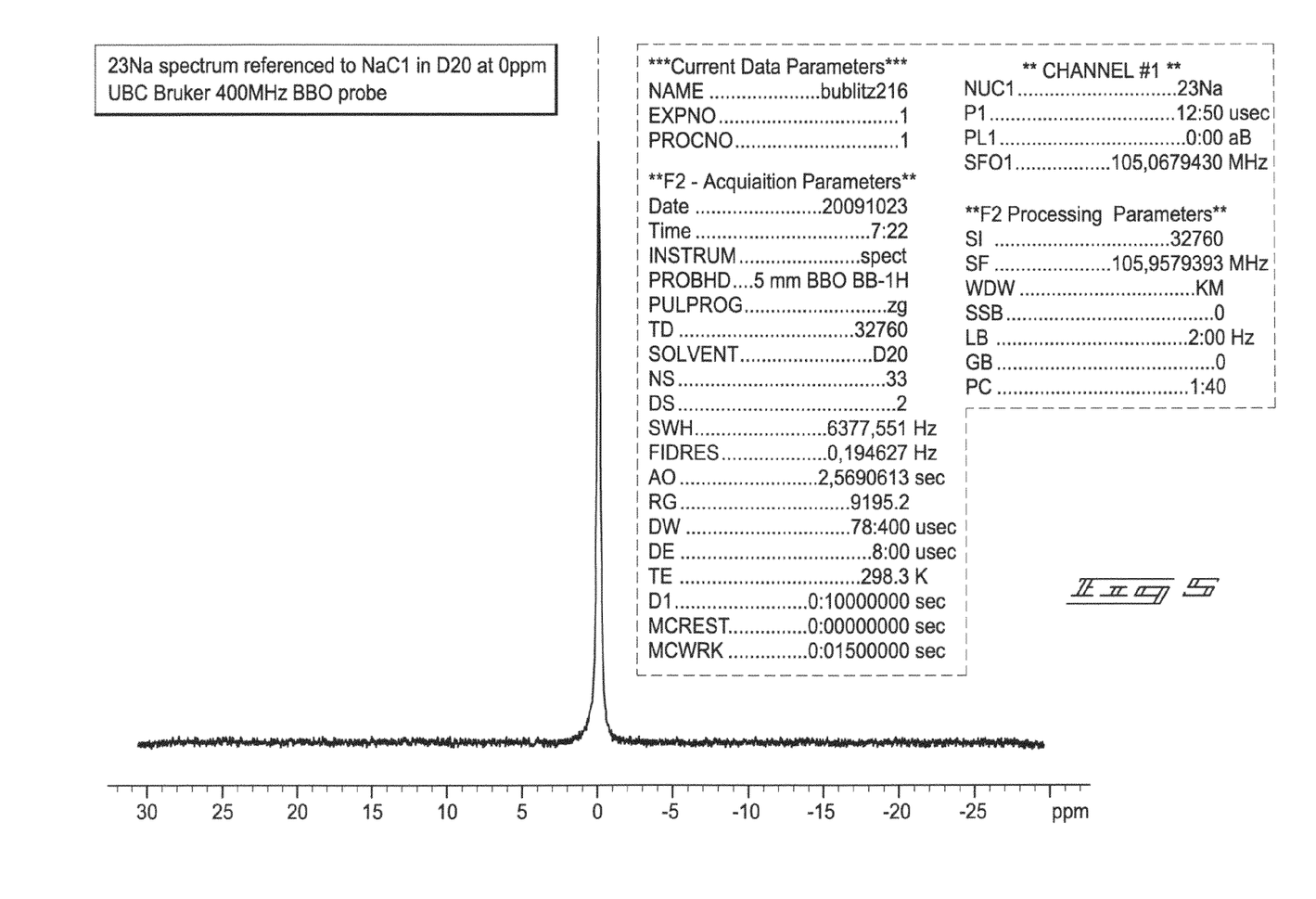
FIG. 5 shows a $^{23}Na$ NMR spectrum of the uppermost fraction product (alcohol soluble fraction) of the invention.

The alcohol/hydride product was analyzed by nuclear magnetic resonance (NMR) spectroscopy $^{23}Na$. As shown in FIG. 5, the $^{23}Na$ NMR spectrum has a single spike, indicative of a single sodium species product. It has been assumed that this is a cationic sodium similar to the sodium in sodium chloride. Accordingly, hydrated electrons must be involved in the structure due to the high basicity of the product liquid. It is theorized that this is where the electromagnetic charge originates and stabilizes the liquid structure.

When the alcohol fraction is added to primary or secondary amines the alcohol fraction creates a stable solution with little or no surface tension. The alcohol product of the invention has the effect of strengthening hydrogen bonds and decreasing the number of hydrogen bonds to stabilize the amine. There is a resulting decrease in vapor pressure and a higher boiling point than either the amine or the alcohol fraction. This is supported by pKa readings of the resulting amine/product mixture.

Although not intended to be bound by theory, it is theorized that the stabilization of amines and hydrogen bonds in general is due to the product's ability to prevent abstraction of hydrogen from a hydrogen bond. Regardless, the ability of the product to stabilize amines and strengthen hydrogen bonds in general is important to the mechanisms of corrosion prevention, oxidation, and interfacial surface tension dynamics.

These factors make the alcohol/hydride product ideal for utilization for amine stabilization in amine processing during gas treatment and fuel creation. The stabilization of amines utilizing the alcohol product of the invention additionally reduces the temperatures at which regeneration can occur thereby lowering the expense of amine regeneration.

The basicity of the alcohol fraction product can play an important role during gas processing and $CO_2$ capture. The basicity prevents acidic protons from being present in the system. Acidic protons present during amine treatment play a role in corrosion, foaming, hydrocarbon saturation, oxygen-salt degradation and product loss; and affects loading and $CO_2$ release during regeneration. The basicity inhibits formation of acid forming compounds, increases loading capabilities, controls deprotonation of ☐witterions reactions, is repulsive to oxygen and sulfur compounds, and effects the temperature of absorption by changing the absorber bulge and maintaining lower temperatures (latent heat).

The product's ability to reduce surface tension is also important during gas treatment and $CO_2$ capture. The lower the surface tension the better the contact for absorption.

for $CO_2$ capture and costs thereof. As shown, the product of the invention (alcohol/hydride product) is economical and efficient.

TABLE I

Current and emerging solvents for $CO_2$ capture

| | Solvent | Solvent loss (kg/ton$CO_2$) | Solvent Cost ($/kg) | Solvent Cost ($/ton $CO_2$) | Steam Use (ton/ton $CO_2$) |
|---|---|---|---|---|---|
| Non-proprietary | MEA | 1 to 3 | 1.30 | 1.3 to 3.9 | 2.0 |
| Econamine[1] | MEA + inhibitors | 1.6 | 1.53 | 2.45 | 2.3 |
| KS-1[2] | Hindered amines | 0.35 | 5.00 | 1.75 | 1.5 |
| PSR[3] | Amine mix | 0.1 to 0.9 | — | — | 1.1 to 1.7 |
| Praxair[4] | Amine mix | 0.5 to 1.5 | 2.00 | 1 to 3 | 1.3 to 1.5 |
| Alcohol/hydride product | Amine mix | 0.1 to 0.2 | 2.80 | 0.35 | 1.1 to 1.3 |

[1]Econamine ™, Fluor Corp. 6700 Las Colinas Blvd. Irving TX 75039.
[2]KS-1 ®, Mitsubishi Heavy Industries, Ltd. Konan 2-chome, Minato-ku Tokyo JAPAN 108-2815.
[3]PSR ™, Amit Chakma.
[4]Praxair ®, Praxair Technology, Inc. 39 Old Ridgebury Rd. Danbury CT 06810

Lower surface tension also produces lower corrosion of metals, lower energy costs in pumping and regeneration, inhibits hydrocarbon saturation in amine mixture, eases water amine separation in regeneration reflux (to prevent amine carryover into reflux water), and inhibits water from exiting with $CO_2$ to create a dry $CO_2$ stream.

The alcohol fraction has the ability to increase solubility of hydrocarbons, thus decreasing hydrocarbon saturation during amine treatment of gases (during amine processing or $CO_2$ capture), which in turn decreases hydrocarbon losses.

Tests of the alcohol fraction product were performed utilizing an amine treatment facility. The tests indicated reduced foaming, decreased corrosion within the system, less oxidation and degradation of the amine, with less polymerization and formation of heat-stable salts, and dry $CO_2$ product stream.

The alcohol fraction or diluted form thereof, may be added to any existing amine absorption process without altering any part of the operation structure. Loading and amine concentrations can be increased. The results include decreased foaming, a significant decrease in process energy utilization and decreased product losses. Thus, the alcohol product is useful for treatment of natural gas, liquid petroleum gas and flue gases with lower amine loss, lower degradation, decreased foaming, decreased corrosion and decreased hydrocarbon saturation. These results allow cost savings due to the ability to utilize lower cost amines, the use of decreased or no defoamers, fewer corrosion inhibitors and longer life of the system, and no need for carbon filters.

Additional advantages afforded with the use of the alcohol fraction product in amine treatment systems include: the ability to use smaller operating facilities due to the ability to utilize increased amine concentration and higher loading; decreased energy usage due to lower heat of dissociation during regeneration; no need for expensive additives; amine life expectancy increased a minimum of tenfold; and $CO_2$ recovery cost reduction of 300% over competitive products without changing existing operational profile.

The alcohol fraction of the invention can be especially useful for $CO_2$ capture due to its ability to produce a dry $CO_2$ product stream, as well as its additional properties set forth above. Table I shows current and emerging solvents utilized The alcohol/hydride fraction is also useful in amine-based absorption of $CO_2$ post combustion from power plant or other emissions ($CO_2$ abatement). The alcohol fraction product can be added in place of water in existing amine circulation systems. The result is reduced foaming, decreased corrosion, decreased hydrocarbon saturation and decreased amine degradation. The alcohol fraction product can be utilized in low-pressure, high carbon dioxide streams with an appropriate amine. Types of gases treated may include but are not limited to liquid petroleum gas, natural gas, coal combustion gas, natural gas combustion gas, diesel combustion gas and oil well flare gas.

In one aspect, the alcohol product can be utilized in concentrated form. In another aspect, the alcohol fraction can be diluted with alcohol prior to use. In another aspect the alcohol fraction or diluted form thereof, can have an appropriate amine or amine mixture added prior to use. Appropriate amines include, for example, MEA, MDEA, DEA, DGA, DTPA, and mixtures thereof. Polypropylene glycol can optionally be added to the mixtures to increase water solubility. Sulfolane can be added to assist in the removal of mercaptans and other sulfur species. It is noted that since the product stabilizes amines and allows easier regeneration, lower cost amines may be utilized in conjunction with the product of the invention.

One example mixture that may be utilized is a mixture of the alcohol fraction (concentrated) with MEA. Uses include, inter alia, utilization as a $CO_2$ scavenger. For example, this product mixture can be utilized in small production gas wells and main gas transportation lines to lower $CO_2$ levels. The product mixture can remove up to two moles of $CO_2$ per mole of product mixture. The product mixture additionally reduces system corrosion (see below).

Another example mixture that can be utilized is 50% concentrated alcohol fraction mixed with 50% triazine. This product mixture can be utilized as an $H_2S$ scavenging liquid. The mixture has a pH of at least 14 with $H_2S$ loading capabilities of up to 4 pounds per gallon of mixture (double the capacity of 100% triazine). The product mixture has a freeze point of below −40° F. which avoids the need to winterize process systems with methanol. This product mixture can be utilized in static mixer designed process systems. The product replaces Sulphatreat® (M-I L.L.C. 5950 North Course Drive, Houston Tex. 77022) and other similar scavenging products that are more expensive.

Considering now the bottom (alcohol insoluble) fraction, such comprises a silica hydroxide liquid compound (at room temperature). The bottom fraction, although insoluble in alcohol an organic solvent, is water-soluble. The silica hydroxide-containing bottom fraction can also be utilized to stabilize amines.

Similar to the alcohol fraction, the bottom fraction can be utilized by addition to amine absorption facilities, mixed with an amine, to treat flue gases, natural gas, liquid petroleum gas, etc. Again, the amine may be a low cost amine due to the stabilization afforded by the product. The use of the product results in lower amine loss, decreased degradation, decreased foaming, decreased corrosion, decreased hydrocarbon saturation and increased cost savings relative to alternative amine treatment systems.

The properties of the bottom fraction in a $CO_2$ capture system include enhanced loading capabilities, higher pH, ease of absorption/desorption which in turn decreases energy requirements, improved product purity (water free $CO_2$), increased amine/water solubility and lower amine loss due to carry over or degradation.

The bottom fraction can additionally be utilized as a scrubbing liquid that can be added to water circulation-spray systems in wet scrubbers to remove contaminants from gas streams. The bottom fraction containing liquid silica hydroxide compound can replace troublesome caustic sodas and solid lime with less expense and higher efficiency. The use of this product decreases or avoids process system corrosion by chemically neutralizing the wet scrubbing environment.

In the scrubbing application, small amounts of hydrogen peroxide, sodium hypochlorite and/or ammonium hydroxide can be added to the bottom fraction product to improve activity without affecting the structure of the product.

It is important to note that, in contrast to traditional lime or calcium hydroxide scrubber additives, the present product does not produce gypsum as a byproduct. The byproduct produced utilizing the bottom fraction in scrubbing processes is a nitride/sulfide-based solid that may be utilized for fertilizers. Corrosion in the scrubbing system is decreased or eliminated thereby extending the life of the system components.

The bottom fraction, when added to a scrubbing system, provides an electrostatic environment. The product hinders the formation of acids (such as $H_2SO_4$) that typically occurs in the wet environment of scrubbing processes. This hindrance is due to the product's ability to affect dispersion forces of non-bonding lone pairs of electrons involved in hydrogen bonding, such as occur in nitrogen, oxygen, sulfur and halogen species. In the presence of the product, high base salts (responsible for degradation) and acids (responsible for corrosion) will be reduced or eliminated.

In another aspect, the bottom fraction can be utilized as part of a mixture in soil washing applications. The mixture can contain from 5% to 50% bottom fraction as an "activator". The mixture can further contain from 20% to 50% of a catalyst such as $H_2O_2$, with any balance being water. The resulting mixture is environmentally safe and can be utilized to destroy harmful hydrocarbon structures from soils and/or water sources.

The methodology for hydrocarbon destruction from soils comprises soaking the soil in the above-described mixture and allowing the mixture to evaporate.

This product mixture can additionally be utilized for creation of hydrogen gas, pressure and heat for down-hole enhancement or oil/sand separation without external heat. The amount of heat and pressure will depend upon the peroxide/bottom fraction ratio.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A method of forming a chemical agent, comprising;
providing solid silicon in a reaction vessel;
adding solid NaOH;
with vigorous mixing, adding a first water ammonium mix to a concentration of two parts water ammonium mix per one part NaOH, the water ammonium mix being 5% ammonium by weight;
reacting for from about 1 hour to about 2 hours at less than or equal to about 195° F.;
adding a second water ammonium mix, the second water ammonium mix being 10% ammonium by weight and being added to maintain the temperature at or below about 195° F. until the final water ratio is 4 parts water to 1 part sodium silicate;
reacting for from about 6 hours to about 8 hours;
adding water until the density reaches about 1.3 specific gravity;
allowing to stand for about 24 hours;
adding an alcohol and mixing vigorously;
allowing to settle; and
collecting an uppermost fraction.

2. The method of claim 1 further comprising adding a catalyst to the reaction vessel.

3. The method of claim 2 wherein the catalyst is selected from the group consisting of Fe—Ni catalysts and Raney nickel.

4. The method of claim 1 wherein the alcohol is ethanol and the uppermost fraction is yellow.

5. The method of claim 1 wherein the solid NaOH is in pellet, prill, or flake form.

6. The method of claim 1 wherein the collected uppermost fraction comprises sodium hydride.

7. The method of claim 1 wherein the alcohol is added to a final concentration of from 10% to 90%, by volume.

8. The method of claim 7 wherein the final alcohol concentration is from about 33% to about 66%, by volume.

9. The method of claim 1 wherein the collected uppermost fraction is an azeotrope.

10. The method of claim 1 further comprising adding monoethanol-amine to the collected uppermost fraction.

11. A method of forming a chemical agent, comprising;
providing solid silicon in a reaction vessel;
adding solid NaOH;
with vigorous mixing, adding a first water ammonium mix to a concentration of two parts water ammonium mix per one part NaOH to form a mixture, the water ammonium mix being 5% ammonium by weight;
reacting for from about 1 hour to about 2 hours at less than or equal to about 195° F.;
adding a second water ammonium mix, the second water ammonium mix being 10% ammonium by weight and being added to maintain the temperature at or below about 195° F. until the final water ratio is 4 parts water to 1 part sodium silicate;

reacting for from about 6 hours to about 8 hours;
adding water until the density reaches about 1.3 specific gravity;
allowing to stand for about 24 hours;
adding an alcohol and mixing vigorously;
allowing to settle; and
collecting a bottom fraction.

12. The method of claim 11 wherein the bottom fraction is black.

13. The method of claim 11 further comprising adding a catalyst to the reaction vessel, the catalyst being selected from the group consisting of Fe—Ni catalysts and Raney nickel.

14. The method of claim 11 wherein the pH of the mixture is greater than or equal to 14.

15. The method of claim 11 wherein the collected bottom fraction has low solubility in organic solvents.

16. The method of claim 11 wherein the collected bottom fraction comprises a liquid silica hydroxide compound.

17. The method of claim 11 further comprising, after the collecting adding one or more of hydrogen peroxide, ammonium hydroxide and sodium hypochlorite to the collected fraction.

\* \* \* \* \*

UNITED STATES PATENT AND TRADEMARK OFFICE
CERTIFICATE OF CORRECTION

Page 1 of 1

PATENT NO. : 8,475,757 B2
APPLICATION NO. : 12/657939
DATED : July 2, 2013
INVENTOR(S) : Mark Owen Bublitz It is certified that error appears in the above-identified patent and that said Letters Patent is hereby corrected as shown below:

Title Page: Item (57) Abstract Line 4 – Replace "of making of amine" with --of making amine--

Title Page: Item (57) Abstract Line 11 – Replace "in anime" with --in amine--

In the Specification:

Column 1, line 48 – Replace "An azeotrope" with --an azeotrope--

Column 2, line 9 – Replace "stage 1." with --stage 1".--

Column 2, line 55 – Replace "flakes prills, or" with --flakes, prills, or--

Column 4, line 64 – Replace "of ☐witterions" with --of zwitter ions--

Column 6, line 43 – Replace "DTPA" with --DIPA--

Column 6, line 53 – Replace "inter alia" with --*inter alia*--

Signed and Sealed this
Third Day of September, 2013

Teresa Stanek Rea
*Acting Director of the United States Patent and Trademark Office*